(12) United States Patent
Choudhry et al.

(10) Patent No.: US 10,265,138 B2
(45) Date of Patent: Apr. 23, 2019

(54) METHODS AND SYSTEMS FOR GENERATING AND USING 3D IMAGES IN SURGICAL SETTINGS

(71) Applicant: MediVis, Inc., New York, NY (US)

(72) Inventors: Osamah J. Choudhry, New York, NY (US); Christopher Morley, Brooklyn, NY (US); Jarrod Phillips, Brooklyn, NY (US); Wenbo Lan, Brooklyn, NY (US)

(73) Assignee: MediVis, Inc., New York, NY (US)

( * ) Notice: Subject to any disclaimer, the term of this patent is extended or adjusted under 35 U.S.C. 154(b) by 0 days.

(21) Appl. No.: 16/033,119

(22) Filed: Jul. 11, 2018

(65) Prior Publication Data

US 2019/0000588 A1 Jan. 3, 2019

Related U.S. Application Data

(60) Provisional application No. 62/560,088, filed on Sep. 18, 2017.

(51) Int. Cl.
| | |
|---|---|
| *G06T 15/08* | (2011.01) |
| *A61B 90/00* | (2016.01) |
| *A61B 34/00* | (2016.01) |
| *A61B 34/10* | (2016.01) |
| *A61B 34/20* | (2016.01) |

(52) U.S. Cl.
CPC .............. *A61B 90/36* (2016.02); *A61B 34/10* (2016.02); *A61B 34/25* (2016.02); *A61B 34/20* (2016.02); *A61B 2034/107* (2016.02); *A61B 2090/365* (2016.02); *A61B 2090/367* (2016.02)

(58) Field of Classification Search
None
See application file for complete search history.

(56) References Cited

U.S. PATENT DOCUMENTS

| | | | | |
|---|---|---|---|---|
| 6,556,199 | B1 * | 4/2003 | Fang | G06T 15/005 |
| | | | | 345/424 |
| 10,102,682 | B1 * | 10/2018 | Samaniego | G06T 19/20 |
| 2005/0219241 | A1 * | 10/2005 | Chun | H04N 13/393 |
| | | | | 345/419 |

(Continued)

OTHER PUBLICATIONS

Palomo et al., "Clinical Application of Three-Dimensional Craniofacial Imaging in Orthodontics", 2005, J Med Sci 2005, 25(6), pp. 269-278 (Year: 2005).*

(Continued)

*Primary Examiner* — Phong X Nguyen
(74) *Attorney, Agent, or Firm* — Bajwa IP Law Firm; Haris Zaheer Bajwa

(57) ABSTRACT

Disclosed herein in a method and system for creating and utilizing a virtual-three dimensional image in a real-world environment to guide medical procedures. The process may include receiving image data related to a patient and creating and displaying a three-dimensional holographic model of the patient utilizing the received image data, wherein creating a three-dimensional holographic model of the patient utilizing the received image data. Exemplary methods include organizing image data in a unique manner and utilizing subvolume skipping techniques allowing for more efficient accurate rendering of holographic images.

19 Claims, 9 Drawing Sheets

(56) References Cited

U.S. PATENT DOCUMENTS

| | | | | |
|---|---|---|---|---|
| 2006/0239554 A1* | 10/2006 | Sun | ............ | G06T 19/00 |
| | | | | 382/173 |
| 2009/0295800 A1* | 12/2009 | Vetter | ............ | G06T 15/08 |
| | | | | 345/424 |
| 2010/0080429 A1* | 4/2010 | Li | ............ | G06T 15/08 |
| | | | | 382/131 |
| 2013/0021336 A1* | 1/2013 | Tsukagoshi | ............ | G02B 27/2214 |
| | | | | 345/419 |
| 2014/0176661 A1* | 6/2014 | Smurro | ............ | G06T 9/001 |
| | | | | 348/14.06 |
| 2015/0049081 A1* | 2/2015 | Coffey | ............ | G06T 19/006 |
| | | | | 345/419 |
| 2016/0106513 A1* | 4/2016 | De Stavola | ............ | A61B 17/15 |
| | | | | 703/1 |
| 2017/0281110 A1* | 10/2017 | Mandelkern | ............ | A61B 6/025 |
| 2018/0165867 A1* | 6/2018 | Kuhn | ............ | B33Y 50/00 |
| 2018/0225861 A1* | 8/2018 | Petkov | ............ | G06T 15/08 |
| 2018/0303558 A1* | 10/2018 | Thomas | ............ | G06F 19/00 |
| 2018/0303563 A1* | 10/2018 | West | ............ | G06T 7/344 |

OTHER PUBLICATIONS

Prieels et al., "Holographic topometry for a dense visualization of soft tissue for facial reconstruction", 2009, Forensic Sci Med Pathol (2009), vol. 5, pp. 11-16 (Year: 2009).*

Virag et al., "Browser-based medical visualization system", 2014, 9th IEEE International Symposium on Applied Computational Intelligence and Informatics, pp. 355-359 (Year: 2014).*

\* cited by examiner

METHODS AND SYSTEMS FOR GENERATING AND USING 3D IMAGES IN SURGICAL SETTINGS

CROSS-REFERENCE TO RELATED APPLICATION

This application claims the benefit of priority from U.S. Provisional Patent Application Ser. No. 62/560,088, filed on Sep. 18, 2017, and entitled "Methods and Systems for Generating and Using 3D images in Surgical Settings," which is incorporated herein by reference in its entirety.

TECHNICAL FIELD

This disclosure relates to an augmented/mixed reality system that generates a virtual three dimensional object, and maps it on to a real life environment. More particularly, the present disclosure related to a method and system for generating accurate three-dimensional (3D) virtual models based on two-dimensional data. The three dimensional-data may then be mapped onto a real-world environment to enable accurate surgical procedures.

The disclosure also relates to methods and systems for providing a wearable and interactive experience by generating the three dimensional (3D) images and additional content in a portable and scalable format.

The disclosure also relates to methods and systems for adjusting and mapping, in real-time, the virtual three dimensional (3D) image in response to detection of user movement of a patient, objects, or a user who is utilizing an augmented reality viewing device.

BACKGROUND

The present disclosure finds its genesis in limitations in using traditional two-dimensional (2D) and 3D images in surgical settings. Surgical planning is necessary for every medical procedure. A surgeon and their team must have a plan for a case before entering an operating room, not just as a matter of good practice but to minimize malpractice liabilities and to enhance patient outcomes. Surgical planning is often conducted based on medical images including 2D DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

While 2D images may allow for a surgeon to make a general plan for a procedure, they have their limitations as the human body is not two-dimensional. Therefore, for complex cases, for example, brain tumor resections, the patient's life and many essential functions are at risk, requiring accurate planning taking into account the three-dimensional complexities of a brain's anatomy. Therefore, there is a need for advancement in visualization that allows for better surgical planning. Currently technology that is being utilized in surgical settings includes traditional monitors which display two-dimensional radiographic imaging co-registered to the patient. Furthermore, current uses of three-dimensional models in medical setting are limited due to their lack of refinement and accurate rendering and an inability to utilize them in real-time with accuracy as a procedure is being conducted.

SUMMARY

An object of the disclosure is to provide new and improved methods and systems for generating and using 3D images for use in medical/surgical settings. The following presents a simplified summary of exemplary embodiments of the present disclosure in order to provide a basic understanding of some aspects described herein. This summary is not an extensive overview of the claimed subject matter. It is intended to neither identify key nor critical elements of the claimed subject matter nor delineate the scope of the subject innovation. Its sole purpose is to present some concepts of the claimed subject matter.

In an exemplary embodiment, a method for navigating a patient using three-dimensional model data. The method comprising generating a three-dimensional model based on patient data. The generated three-dimensional model data may then be co-registered with the patient based on receiving data related to a real-world environment.

In an exemplary embodiment, a method for utilizing a virtual-three dimensional image in a real-world environment to guide medical procedures, comprising receiving image data related to a patient, wherein the image data includes a plurality of Digital Imaging and Communications in Medicine (DICOM) files and associated metadata for the plurality of the DICOM files, and creating and displaying a three-dimensional holographic model of the patient utilizing the received image data. Creating a three-dimensional holographic model of the patient utilizing the received image data comprises sorting the plurality of DICOM files according to an order of their physical location, acquiring raw image data for each of the respective slices associated with each of the plurality of DICOM files, reorienting the raw image data based on physical orientation associated with each of the respective slices and placing the raw image data for each of the respective slices in a first integer array, the first integer array containing image data associated with every slice in the scan, and splitting respective number of pixels in the first integer array associated with respective subcubes of a first size, creating a second integer array by splitting the first integer array into subvolumes, wherein each respective subvolume contains a plurality of subcubes and wherein each subvolume of the plurality of subvolumes in the second integer array contains a largest value of its corresponding subcube of the first integer array. It may further include creating a 3D texture using the first integer array, creating a 3D cube mesh that is sized based on physical dimensions of the scan, and rendering a three-dimensional holographic model of the patient based on the 3D texture and the 3D cue mesh by utilizing ray-casting approaches.

The three-dimensional hologram model to be displayed in a real-world environment may be any suitable display device which may display mixed or augmented reality as discussed in the embodiments.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which.

DETAILED DESCRIPTION

The novel features which are believed to be characteristic of the present disclosure, as to its structure, organization, use and method of operation, together with further objectives and advantages thereof, will be better understood from the following discussion.

It may be understood that when used herein, the term "the three dimensional (3D) image" or "3D image" may be an actual 3D image or may be 3D hologram or an image that is created based on generation and display of a two-dimensional (2D) image.

In an exemplary embodiment, an exemplary method may include creating a three-dimensional model of a patient utilizing patient data. The steps may include converting patient image data such as MRI, CT, or additional medical imaging related pixel data into holographic voxel data. In exemplary embodiments, computational verification of volumetric rendering may be utilized to ensure mathematical accuracy. Volumetric rendering may rely on appropriately solving an equation known as the volume rendering integral (VRI) through a procedure known as volume ray-casting. In volume ray-casting, a ray starting at a pixel position directed towards the volume may be discretized into sample points. The sample points may then be evaluated according to transfer functions, and, lastly, may be combined into one value via numerical integration.

In an exemplary embodiment, once an accurate holographic model is generated utilizing the exemplary methods, the holographic model may then be co-registered with a patient in a real-world environment such as a surgical setting. For example, holographic rendering of a patient's MRI or CT scan may be co-registered to point cloud information being generated. In exemplary embodiments, point cloud information may refer to information related to a set of data points in space, for example, in surgical settings. With movement of the point cloud, corresponding movement of the holographic rendering may also be accounted for according to exemplary methods. Such holographic co-registration of medical imaging would work in all settings including any operating room or the bedside as all would be required is image data from a small stereoscopic Infrared camera that may be mounted on an augmented reality viewing device. In exemplary embodiment, additional types of image capturing device may be mounted on an augmented reality viewing device. In exemplary embodiments, the augmented reality viewing device may be a wireless and wearable unit.

Figure 1A:
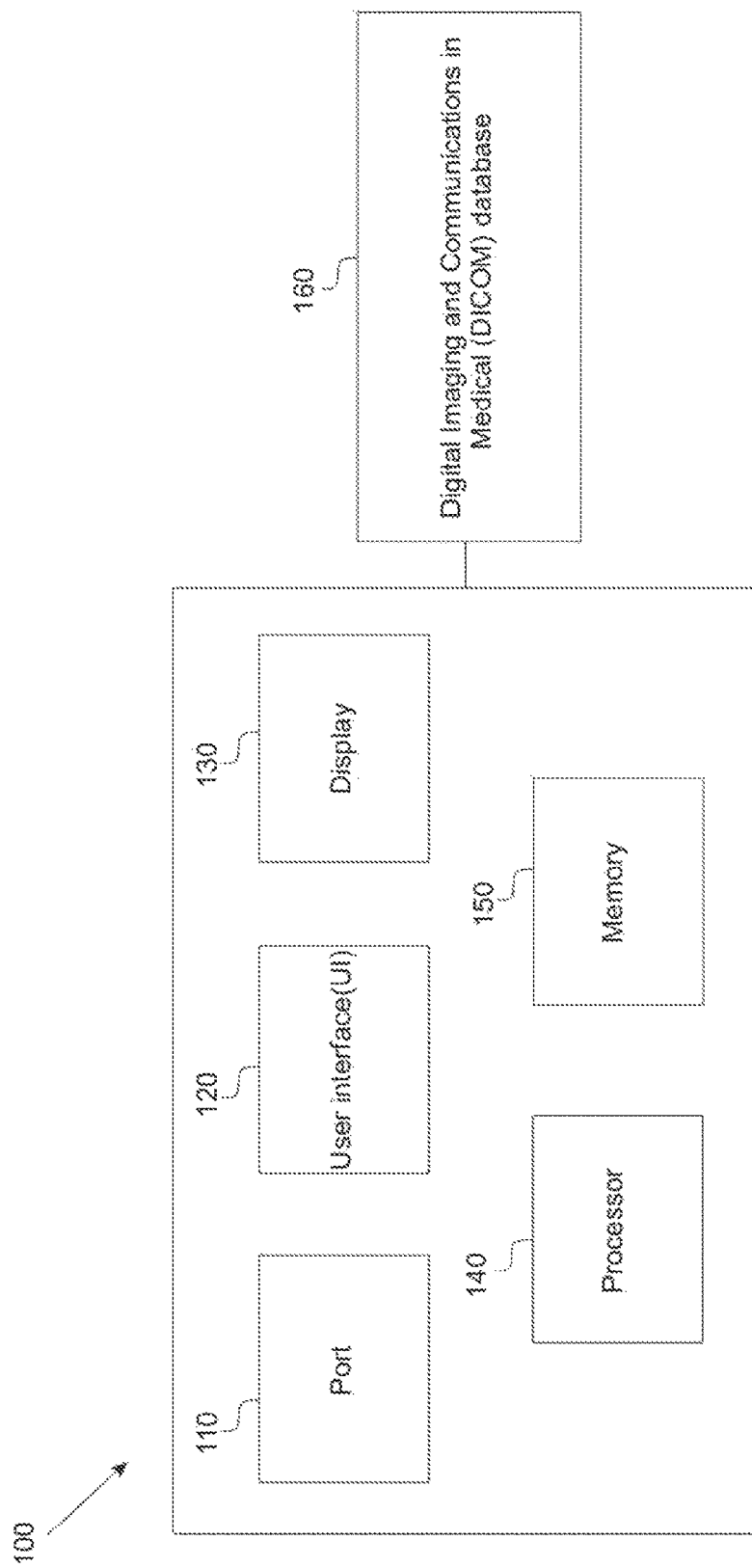
FIG. 1A is a block diagram illustrating a configuration example of a medical image processing device, consistent with one or more exemplary embodiments of the present disclosure.

FIG. 1A is a block diagram illustrating an exemplary configuration of a medical image processing device 100, consistent with one or more exemplary embodiments of the present disclosure. The medical image processing device 100 may include a port 110, a user interface (UI) 120, a display 130, a processor 140, and a memory 150. The medical image processing device 100 may be connected to a Digital Imaging and Communications in Medicine (DICOM) database 160. The medical image processing device 100 may retrieve or receive DICOM files from DICOM database 160 and may use these files to volumetrically render a holographic image of a patient utilizing methods described in further detail below. In exemplary embodiments, database 160 may be a local memory or a PACS server.

The port 110 may acquire or retrieve the DICOM files or similar medical images. The acquired DICOM files may be immediately sent to the processor 140 and may be subjected to various processes therein, or may be stored in the memory 150 and may then be sent to the processor 140 and subjected to various processes therein, if necessary.

The display 130 may be an augmented/mixed reality device. Furthermore, display 130 may refer to a plurality of displays. Accordingly, in an exemplary embodiment, a holographic model may be rendered utilizing a wearable augmented/mixed reality device while at the same time being displayed on another display device, including, for example, a liquid crystal display (LCD). Display 130 may be configured to display a variety of information including various volume rendering images. The displayed images may include colored ray casting images, in addition to colored MIP images and other colored volume rendering images.

The UI 120 may be one of a touch panel, a pointing device, a keyboard, a voice input, or additional user input devices. The UI 120 may be configured to receive an arbitrary input operation from a user (for example, a doctor, a radiological technologist, surgeon, or a radiologist) of the medical image processing device 100. In exemplary embodiments, display 130 may serve as a user interface as well. For example, if display 130 is an augmented reality viewing device, display 130 may relay information related to head location, head movement, gestures, etc.

The memory 150 may include a read only memory (ROM) or a random access memory (RAM). The memory 150 may store a variety of information or programs. The variety of information includes, for example, images generated by the processor 140, and setting information set by the processor 140.

The processor 140 may include one or more of a central processing unit (CPU), a digital signal processor (DSP), or a graphics processing unit (GPU). The processor 140 may perform various processes or control by executing various programs stored in the memory 150. The processor 140 may control the constituent units of the medical image processing device 100. In exemplary embodiments, processor 140 may generate a color volumetric rendering from the DICOM files.

Figure 1B:
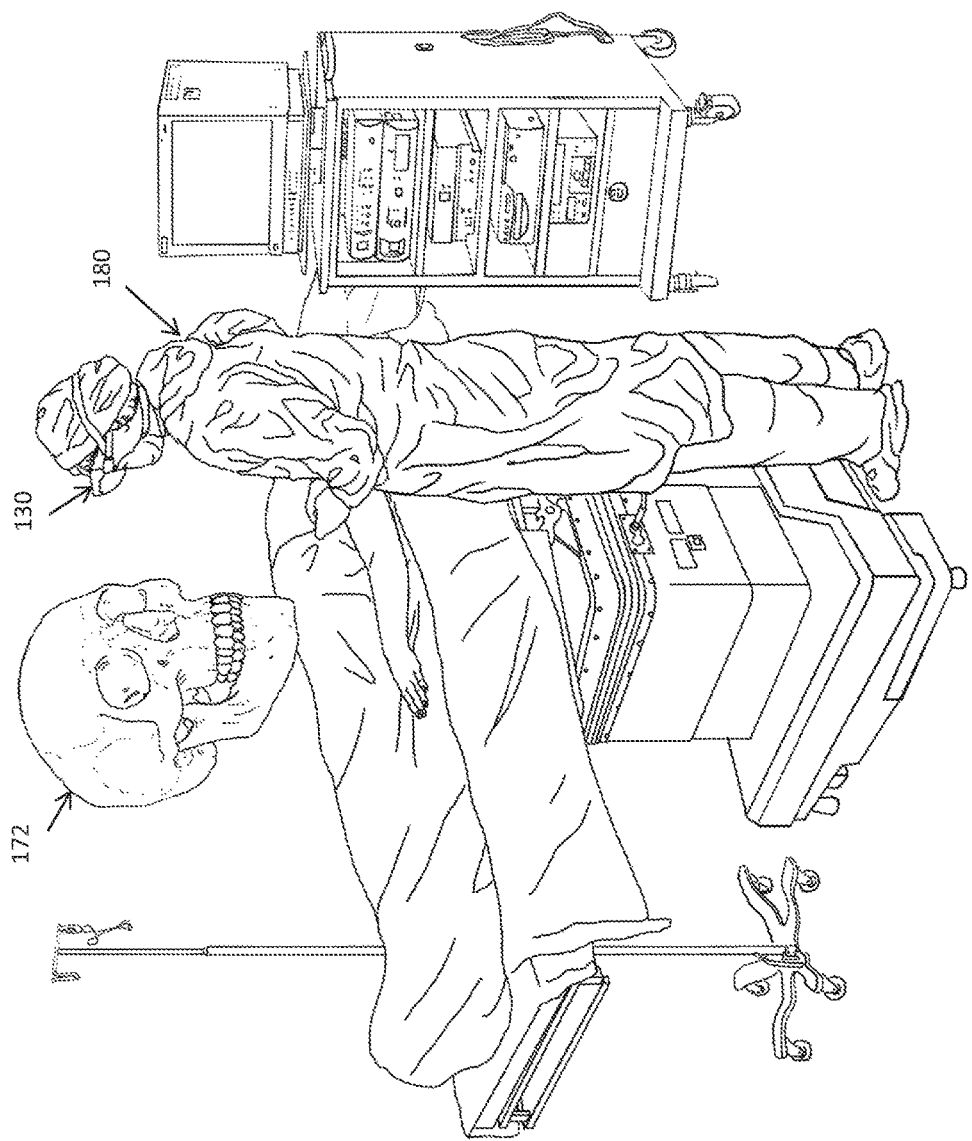
FIG. 1B illustrates an environment in which the medical image processing device may be utilized, consistent with one or more exemplary embodiments of the present disclosure.

FIG. 1B illustrates an environment 170 in which the medical image processing device 100 may be utilized, consistent with one or more exemplary embodiments of the present disclosure. Specifically, environment 170 displays a user 180 wearing an exemplary display device 130, which may be an augmented reality display device. A holographic rendering 172 (in this example, a rendering of an exemplary brain) viewable only through display device 130 or similar display devices is illustrated in context of environment 170. In exemplary embodiments, holographic rendering 172 may retain its position from the perspective of user 180. Accordingly, as user 180 moves around in environment 170, user 180 may view different perspectives of holographic renderings. Additionally in exemplary embodiments, using gestures or other user inputs, user 180 may be able to change sizes, layers, perspectives, orientation, etc., of holographic rendering 172. This may be an important aspect when holographic rendering 172 is being used for reference or for enhancing understanding of part of parts of a human body represented by holographic rendering 172. For example, it may be important for a surgeon to know the outside perspective of the brain but also to be able to visualize aspects and status of the brain on the inside layers. In an exemplary embodiment, holographic rendering 172 may retain its actual size and may be overlaid over an exemplary patient in environment 170. Accordingly, holographic rendering 172 may be utilized for guidance during surgical or additional medical procedures.

An operational example of the medical image processing device 100 will be described below with respect to FIGS. 2-4.

Figure 2:
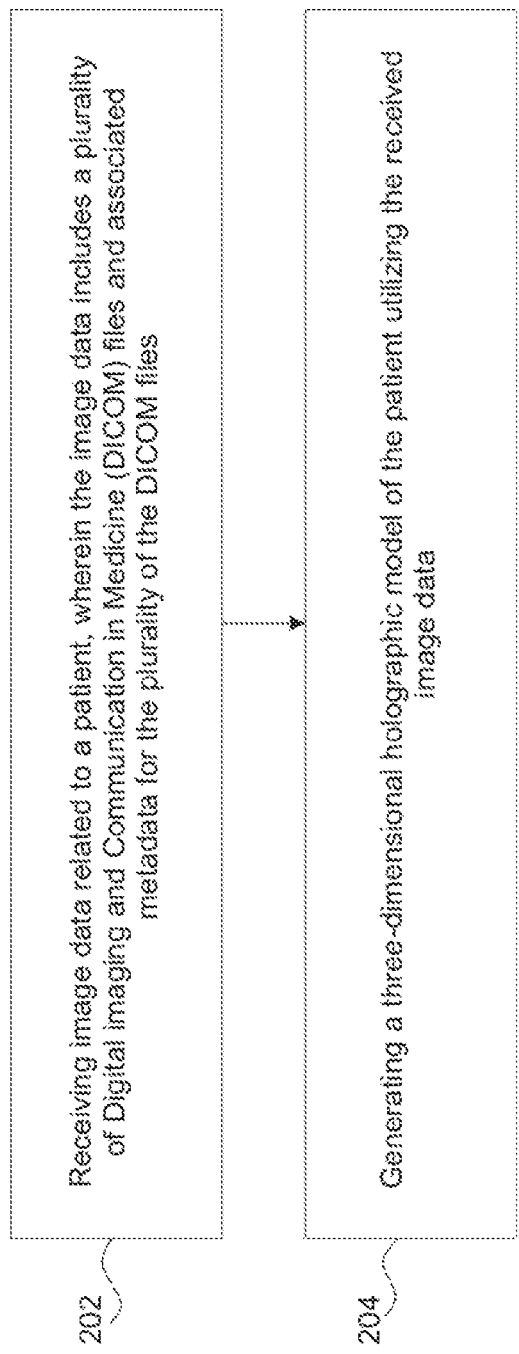
FIG. 2 illustrates a method utilizing a virtual-three dimensional image in a real-world environment to guide medical procedures, consistent with one or more exemplary embodiments of the present disclosure.
Figure 3:
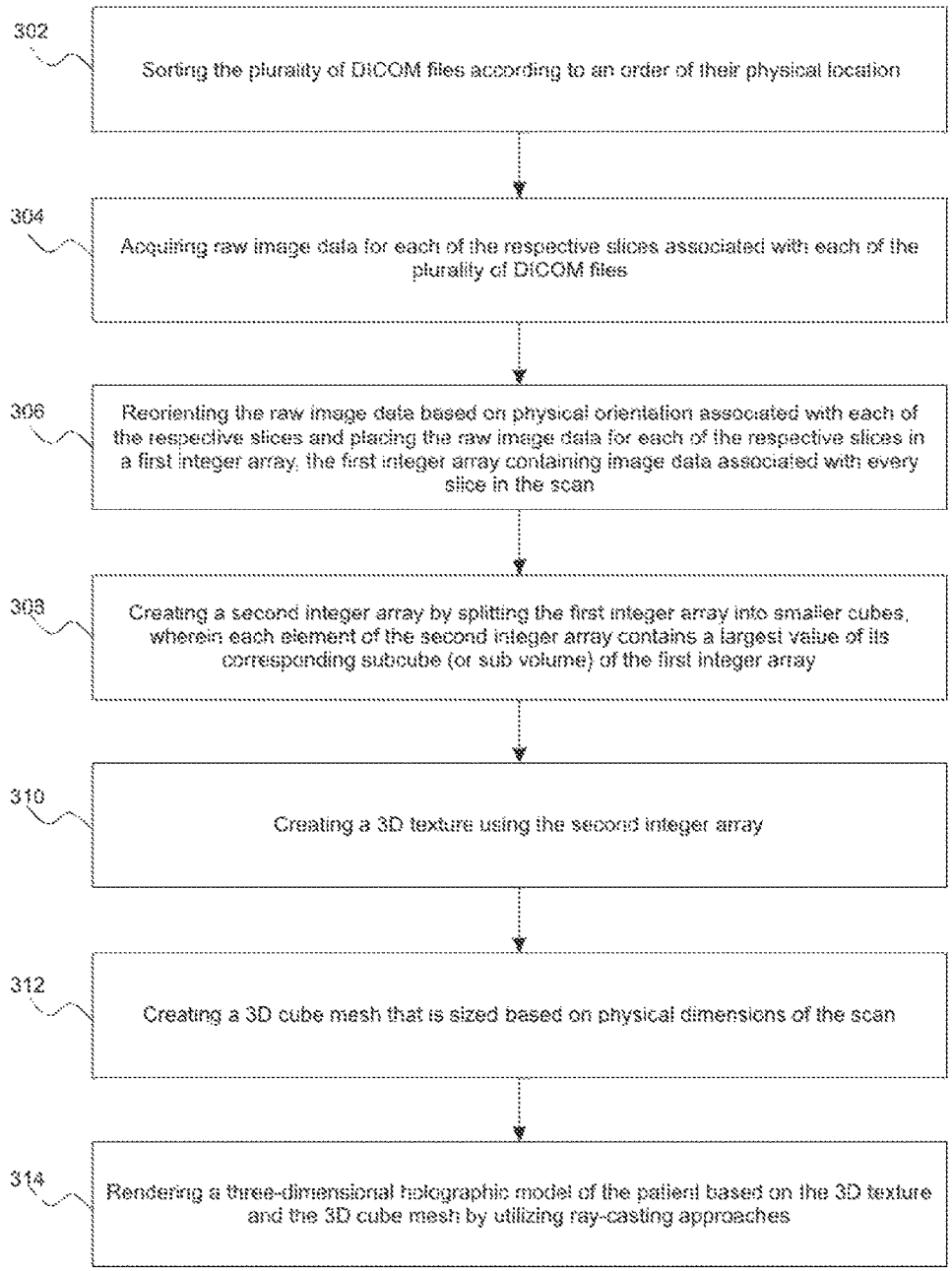
FIG. 3 illustrates a method for creating a three-dimensional holographic model of the patient utilizing the received image data, consistent with one or more exemplary embodiments of the present disclosure.

FIG. 2 illustrates method 200 for utilizing a virtual-three dimensional image in a real-world environment to guide medical procedures, consistent with one or more exemplary embodiments of the present disclosure.

Step 202 may comprise receiving image data related to a patient. In an exemplary embodiment, the image data may include a plurality of Digital Imaging and Communications in Medicine (MOM) files and associated metadata for the plurality of the DOOM files. Each DICOM file may represent a slice from a single scan of an exemplary patient. In exemplary embodiments, these files may be stored locally on disk or obtained from a picture archiving and communication system (PACS) server, such as DICOM database 160.

In exemplary embodiments, metadata associated with the plurality of DICOM files may include, but is not limited to, image resolution, physical orientation of the slice, physical dimensions of each pixel, binary encoding format of the data, patient information, scan modality, and physician information. In exemplary embodiments, some metadata may be assumed to be identical for each slice, while other metadata may be unique per slice. For example, certain information such as patient name, basic patient information, time that data is captured, may be similar across each slice. However, metadata related to the physical location of each of the captured slides in a scan may be unique.

Step 204 may include generating a three-dimensional holographic model of the patient utilizing the received image data. FIG. 3 illustrates an exemplary method 300 for creating a three-dimensional holographic model of the patient utilizing the received image data, analogous to step 204 of method 200, consistent with one or more exemplary embodiments of the present disclosure.

Figure 5:
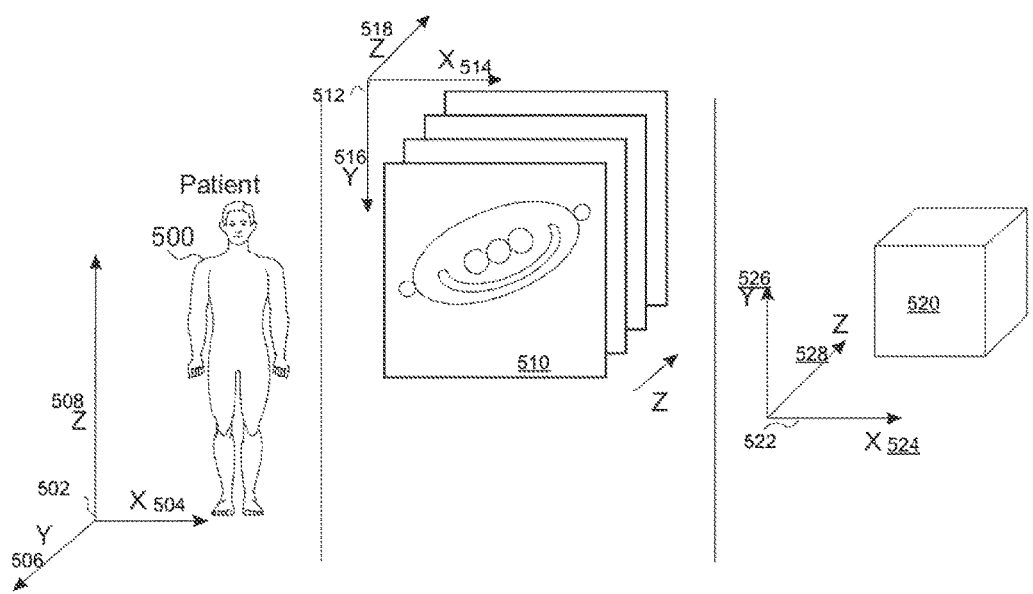
FIG. 5 illustrates orientations in different settings, consistent with one or more exemplary embodiments of the present disclosure.

Step 302 may include sorting the plurality of DICOM files according to an order of their physical location. Specifically, using physical location information from the metadata (for example, the instance number tag), the files may be sorted in order of physical location, starting with the lowest part of the body and going to the highest. In exemplary embodiments, the sorting from the lowest part of the body may not be necessary if the physical location is accounted for when the raw data is reoriented during a later step in method 300. In exemplary embodiments, patient orientation may be described with three separate axes: X, Y, and Z. The patient's left-right axis is the X axis, with the value of X increasing from left to right. The patient's forward-backward axis is the Y axis, with the value of Y increasing from front to back. The patient's up-down axis is the Z axis, with the value of Z increasing from foot to head. FIG. 5 illustrates orientations in different settings, consistent with one or more exemplary embodiments of the present disclosure. Specifically, for patient 500, orientation 502 displays orientations for x-axis 504, y-axis 506, and z-axis 508.

On the other hand, DICOM files have their own orientation scheme wherein the X axis in each image starts on the left and increases in the right direction. The Y axis in each image increases from the top of the image to the bottom of the image. The Z axis is indicated by the slices themselves. For exemplary image stack 510 (which may contain DICOM files), orientation 512 displays orientations for x-axis 514, y-axis 516, and z-axis 518. In exemplary embodiments, image stack 510 may represent an image related to patient 500, but the orientation is different due to the manner orientations are recorded in the context of DICOM files. In exemplary embodiments, these orientations are important because the exemplary target rendering engine to be discussed in further detail below uses the Y-axis for up-down and Z-axis for front-back of a patient. Rendering Engine Orientation 522 displays orientations for x-axis 524, y-axis 526, and z-axis 528, for an exemplary rendering engine display 520. Exemplary engine display 520, merely is an illustrative box for explaining the context of orientations. One of ordinary skill in the art, would comprehend that it refers to any displays rendered according to exemplary embodiments of the present disclosure. Accordingly, the differences in orientations between an exemplary patient, exemplary image stack, and an exemplary rendering engine need to be accounted for in order to generate a correctly oriented 3D render because the patient may not always face the same direction in a scan. Specifically, the scan may be a side view, top-down view, or front view of the patient. In exemplary embodiments, the difference in orientation may also be accounted for during the rendering process but accounting for it during the import process simplifies rendering. Specifically, the exemplary conversion may also happen during the rendering process, but that approach may require conversion for each rendered frame, therefore, increasing the amount of processing required at that later stage. Accordingly, exemplary methods are more efficient accounting for orientation during an exemplary import process. Essentially, the orientations may be changed at this stage to correspond to the spatial axis orientations used by the exemplary rendering engine.

In exemplary embodiments, the exemplary rendering engine consistent with the present disclosure may utilize textures with resolutions that are an exact power of two. Accordingly, if the X, Y, and Z resolutions aren't an exact power of two, the resolutions may be changed to the next largest power of two. In exemplary embodiments, when utilizing rendering engines where such resolution is not required and where the rendering engine may accommodate non-power of two textures, such modification may not need to be utilized.

Step 304 may entail acquiring raw image data for each of the respective slices associated with each of the plurality of DICOM files. Specifically, as discussed above, each exemplary DICOM file corresponds to a respective slice from a single scan of a patient. In exemplary embodiments raw image data may refer to intensity/density of each pixel.

Step 306 may entail reorienting the raw image data based on physical orientation associated with each of the respective slices and placing the reoriented raw image data for each of the respective slices in a first integer array, the first integer array containing image data associated with every slice in the scan. In detail, the physical orientation information from the metadata of respective slices (which for example, may be used for step 302 for ordering the slices) may be utilized to reorient the data when it is placed it in the scan array. This step may be processed on a central processing unit or any processor on which software instructions and calculations may be performed. Alternatively, the data may be passed to a graphics processing unit-a specialized piece of hardware used to render 3D geometry where it may be processed much faster. In exemplary embodiments, if the texture resolution is upsized in step 302, the "extra" parts of the array may be filled with zeroes.

Step 308 may entail creating a second integer array that is representative of the first integer array, wherein each element of the second integer corresponds to the largest element within a grouping of elements from the first array. This grouping of elements represents a smaller cube within the larger cube represented by the full array. In exemplary embodiment, this process may be performed on an exemplary CPU or GPU.

Figure 6A:
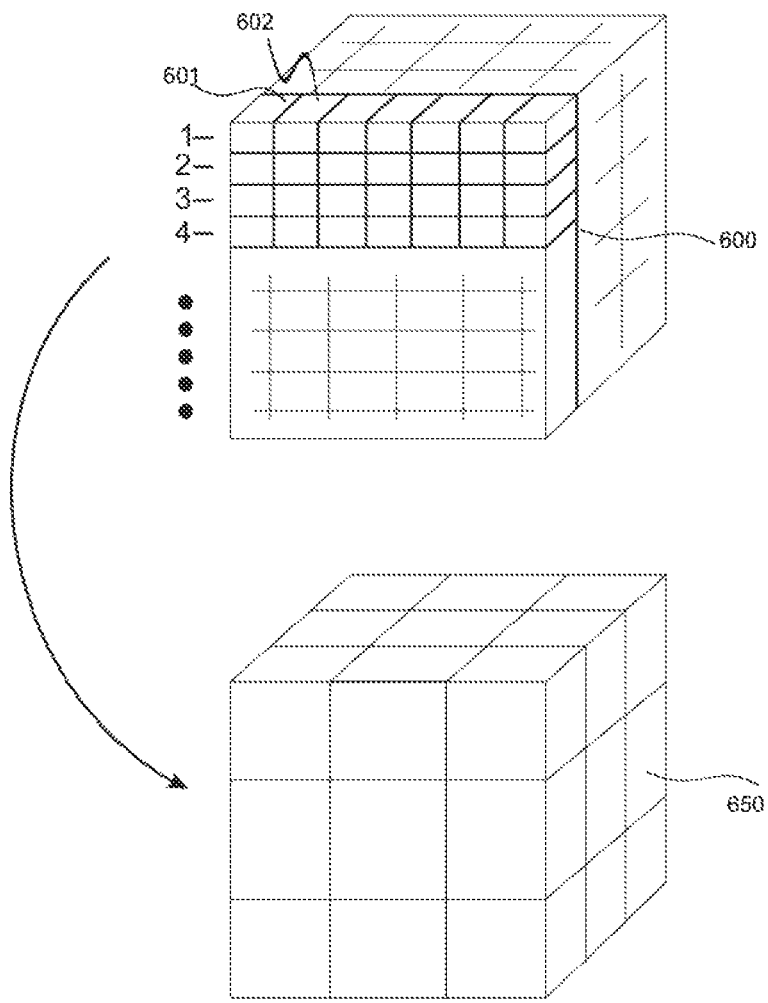
FIGS. 6A and 6B illustrate representative creation of an exemplary second integer array from a first integer array, consistent with one or more exemplary embodiments of the present disclosure.
Figure 6B:
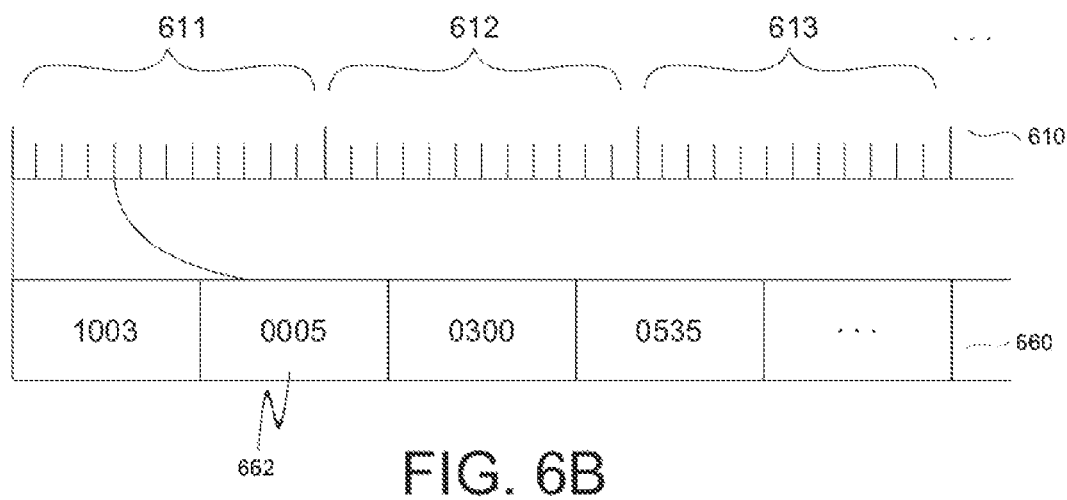

In an exemplary embodiment, the second integer array may represent groupings of pixels from the first array. In an exemplary embodiment, the entire first array as a whole represents a cube or a volume and each element in the second array represents a subdivision of the first array. For example, if the first integer array represents a 32×32×16 cube, exemplary subvolumes may represent 4×4×4 subdivisions of the original cube. In this exemplary scenario, the second array may be an 8×8×4 cube. In exemplary embodiments, the sub volumes may evenly divide the dimensions of the original cube. In exemplary embodiments, there may be 8 subcubes from each respective cube. FIGS. 6A and 6B illustrate representative creation of an exemplary second integer array from a first integer array, consistent with one or more exemplary embodiments of the present disclosure. Cube 600 contains values associated with a plurality of slices (1, 2, 3, . . . n). First integer array 610 represents an exemplary integer array associated with cube 600. Specifically, each part of the integer array represents a corresponding value from cube 600. For example, 611 may correspond to box 601, 612 may correspond to box 602, etc. Cube 650 displays cube 600 split in a plurality of subcubes. Furthermore, second integer array 660 represents an exemplary integer array generated based on first integer array 610. For example, part 662 of second integer array may correspond to part 611 of first integer array 610. Furthermore, cube 650 illustrates an exemplary volume split into subvolumes. In exemplary embodiments, cubes 600 and 650 may be associated with the same image volume. However, subvolumes of cube 650 may be larger than subcubes of cube 600. Accordingly, a size of an exemplary subvolume may correspond to a plurality of subcubes.

Step 310 may entail creating 3D textures using the second integer array. In exemplary embodiments, the 3D texture may be a single channel texture if the scan is black and white, or it may be a 4 channel texture (red, green, blue, and alpha) if the scan is in color. In an exemplary embodiment, the integers in the source integer array may be divided by some normalizing value to convert each of the respective integers into a float with a value ranging from 0 to 1. The normalizing value must be larger than the largest value in the scan. The normalization process may be completed on the GPU or the CPU.

Step 312 may entail creating a 3D cube mesh that is sized based on physical dimensions of the scan. Specifically, an exemplary 3D cube mesh may be reflective of physical features of a patient (in physical dimensions). Therefore, this information along with the 3D texture may be utilized to render a volumetric representation of a patient as discussed in further detail below.

In exemplary embodiments, method 300 may further include creating a histogram representing the values in the primary integer array. This histogram may be used as a reference when making a color lookup table.

In exemplary embodiments, method 300 may further include passing the 3D texture to an exemplary GPU after its finished building.

Step 314 may entail rendering a three-dimensional holographic model of the patient based on the 3D texture and 3D cube mesh by utilizing ray-casting approaches. In exemplary embodiments, majority of the rendering occurs on a pixel shader on the GPU. In exemplary embodiments, a shader is software that may be used when processing graphics and it computes color and other graphic attributes of a pixel Essentially, a shader is a program that tells the GPU how a 3D object should appear on a display, such as a computer screen. An exemplary pixel shader periodically performs a series of calculations for each visible pixel on the surface of the cube. The end goal of these calculations is to turn the colors stored in the 3D texture into a three dimensional representation of the scan. This may be accomplished by traversing along a ray that starts at the camera and passes through each visible surface pixel on the 3D cube mesh. Colors are sampled from the 3D texture along the length of this ray and blended together to produce a single output color for each surface pixel. In exemplary embodiments, there are two sets of coordinates to consider when talking about physical location during the raymarching process. The first set of exemplary coordinates may be object coordinates that are centered on the cube mesh. The units for the exemplary object coordinates may be in meters. The second set of exemplary coordinates may be texture coordinates that are centered on the front right bottom corner of the texture. Each dimension of texture coordinates may a floating point number between 0 and 1, which represents the percentage from the starting edge of the texture to the opposite edge. This system may be used to determine the sampling point on the texture.

In exemplary embodiments, one set of coordinates may be converted to the other. There may be a handful of periodic calculations that may be easier to perform on the CPU because their results are identical for each pixel being rendered. These results may be passed to the GPU each frame. In exemplary embodiments a first CPU rendering calculations may entail using a cross-section plane that is attached to a virtual object in an exemplary scene. In such a scenario, a linear equation is created for the plane in the form ax+by +cz+d. If it is assumed that the unit vector (a,b,c) is the direction the plane is facing, then the scalar d is the dot product of (a,b,c) and some point on the plane. Since the physical location of the plane is known in object space, it may be used to determine d. However, this point must be converted to texture coordinates before calculating d because the shader calculations primarily occur in texture coordinates. On the other hand, if view-aligned ray marching is being performed, an arbitrary plane may be generated to use as the basis for an exemplary view-aligned ray marching process. The related calculations for view-aligned ray marching need the plane's normal vector (a unit vector that represents the facing direction of the plane) and a position on the plane. The normal vector may either be the camera's forward facing direction or a unit vector from the camera to the center of the 3D cube mesh, both in object space. The center of the cube or the point on the cube nearest to the camera may be used for the plane point, but both must be converted to texture coordinates. Any combination of those two normals and points may be used, as they allows for a manner of describing two sets of parallel planes.

Figure 4A:
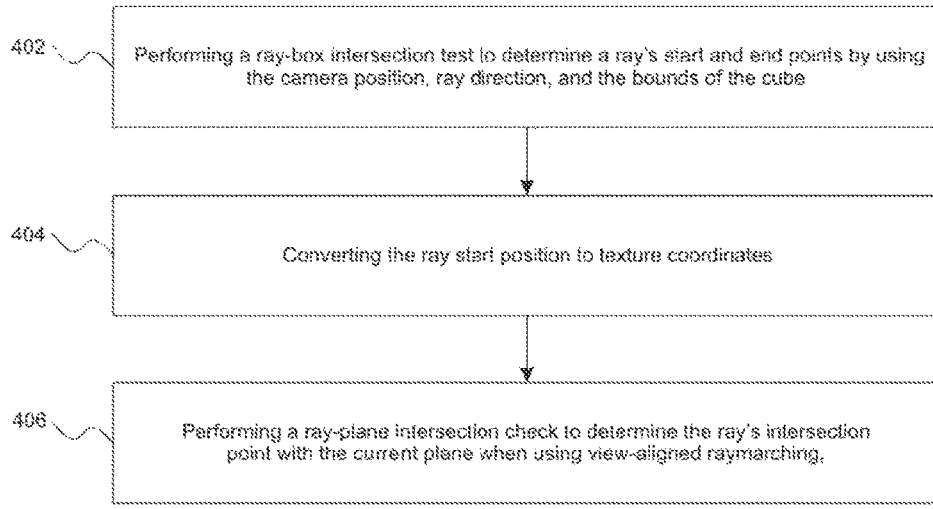
FIGS. 4A and 4B illustrates methods for raymarching, consistent with one or more exemplary embodiments of the present disclosure.

FIG. 4A illustrates method 400 for raymarching, consistent with one or more exemplary embodiments of the present disclosure. In exemplary embodiments, method 400 may be repeated for each sub volume along the ray unless the maximum color threshold has been exceeded or the ray has exited the volume. In exemplary embodiments, the color threshold may be a high value that indicates the ray has passed through a solid object. As the ray interpolates colors as it passes through the volume, the value would be exceeded when it accumulates enough color to exceed this threshold.

Step 402 may entail performing a ray-box intersection test to determine a ray's start and end points by using the camera position, ray direction, and the bounds of the cube. In exemplary embodiments, the bounds of the cube may be adjusted in order to crop out sections of the cube, In an exemplary embodiment, cropping out sections of the cube allows to focus user attention on relevant parts of a patient. If an exemplary scenario, when camera distance based clipping plane is utilized, a maximum of the clip plane distance and the ray start distance may be used to determine where to start the ray.

Step 404 may include converting the ray start position to texture coordinates.

If a view-aligned raymarching is being utilized, the process may include performing a ray-plane intersection check using the reference plane normal as both direction vectors to determine the distance from the start point to the reference plane that was set by the CPU. Then this distance may be rounded off to the nearest ray step distance and then utilized to step back from a reference view plane's position (along the plane normal, not the ray direction). This process provides the position of the start plane for this ray. In an exemplary embodiment, to find the position of next view plane, the process may include multiplying the ray step distance by the plane normal to get a vector that allows us to find the position of next view plane (referred to as the plane step vector).

In another exemplary scenario, if view-aligned raymarching is not being utilized, then the process may include multiplying the ray step length by the ray direction to get a vector that allows for finding the next sample point.

For both exemplary scenarios, a distance between the start and end points of the ray may be determined.

Step 406 may entail performing a ray-plane intersection check to determine the ray's intersection point with the current plane when using view-aligned raymarching. Then adding the plane step vector to the current plane point may be used to find the next plane. In exemplary embodiments, when not using view-aligned raymarching, a ray's current position may be used as the sample point. In embodiments, when using a cross-section plane that is attached to a virtual object in the scene, a dot product of a plane equation and the ray position may be utilized to determine the ray's position relative to the plane. Responsive to determining a negative result, the voxel color may be ignored. By ignoring voxels on one side of the virtual plane, a cross-sectional view of anatomical structures inside the scan may be produced. Otherwise, when the result is positive, sample the color from the 3D texture at that point, perform windowing calculations (a DICOM term for brightness and contrast) if necessary, and blend the color with the colors that have already been sampled along the ray.

In an exemplary embodiment, when using a lookup texture, the color from the 3D texture is used to sample the lookup texture and blended with the colors that may already been sampled. Step 406 is repeated until the accumulated color exceeds a predetermined value or the ray exits the current volume.

Figure 4B:
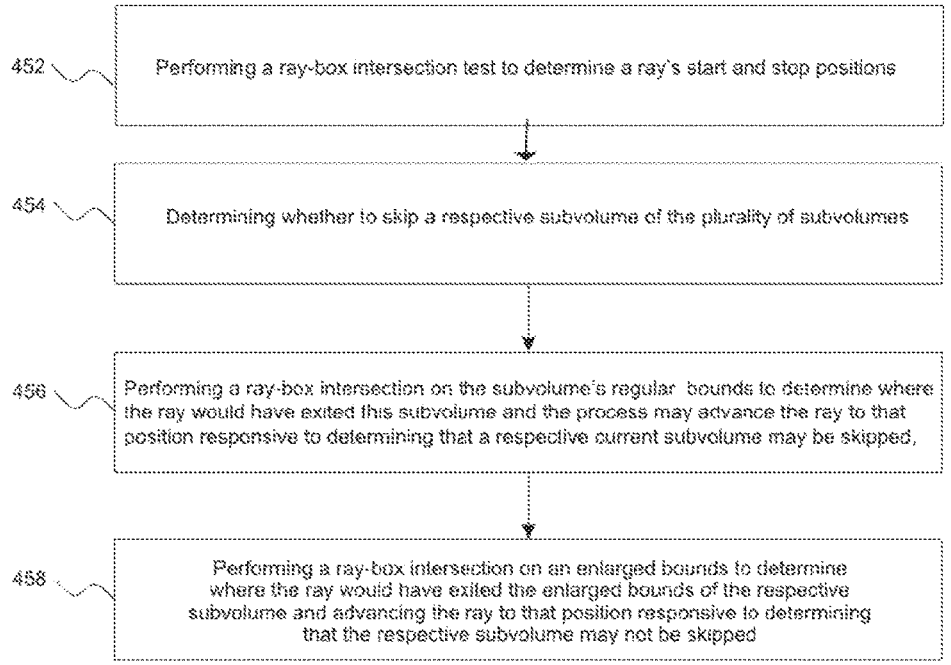
Figure 7A:
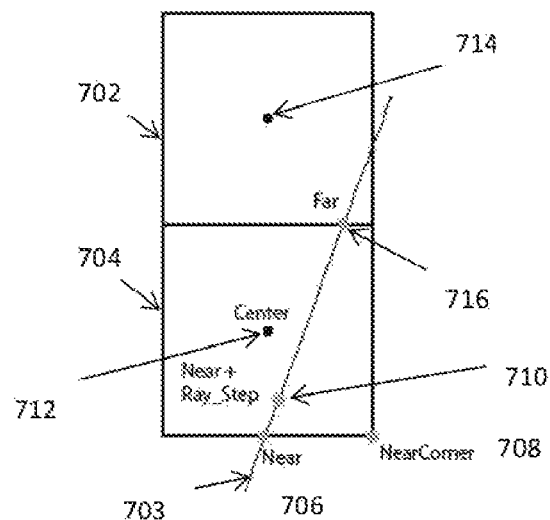
FIGS. 7A and 7B illustrate exemplary scenarios of exemplary subvolumes utilizing regular bounds and enlarged bounds, consistent with one or more exemplary embodiments of the present disclosure.
Figure 7B:
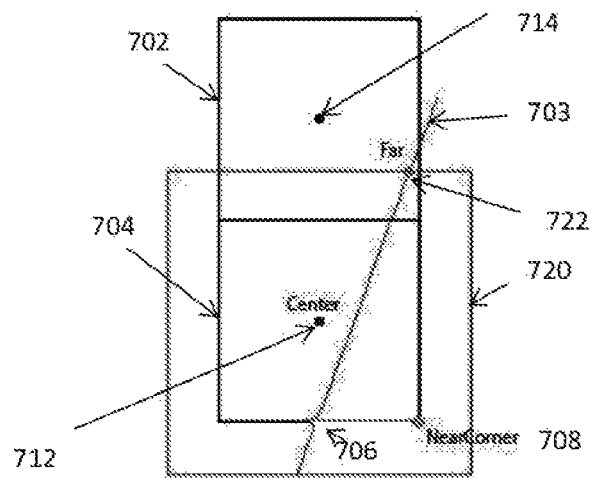

FIG. 4B illustrates method 450 for utilizing enlarged subvolmes for raymarching, consistent with one or more exemplary embodiments of the present disclosure. FIGS. 7A and 7B illustrate exemplary subvolumes utilizing regular bounds and enlarged bounds, consistent with one or more exemplary embodiments of the present disclosure. In an exemplary embodiment and for purposes of explanation, an exemplary three-dimensional texture representation of a full DICOM scan may be referred to as the volume.

Using exemplary methods discussed above, an exemplary three-dimensional subvolume texture may be created during scan import. Each voxel in the exemplary texture may be a proxy for the highest value in a cubic area from the main volume. This proxy texture may help expedite the raymarching process since it may be assumed that a subvolume with sufficiently low density is empty. Empty subvolumes are completely transparent, therefore, they may be skipped and the process may move the ray sampling position to the next subvolume along the ray.

In an exemplary embodiment, when determining the highest value in a cubic area from the main volume, an additional voxel may be added to each face of an exemplary subvolume's dimensions so that adjacent subvolumes overlap with each other. Accordingly, enlarged bounds may be created for a respective subvolume by adding a voxel to each side. So if an 8×8×8 subvolume is being constructed, the process may actually find the highest value in a 10×10×10 area in the main volume. This enlargement (referred to as using "enlarged bounds") aids in making the raymarching process more efficient as explained in further detail below.

Step 452 may entail performing a ray-box intersection test to determine a ray's start and stop positions utilizing aspects of using the camera position, ray direction, and/or the bounds of the cube similar to aspects of step 402.

As explained in further detail below, these positions may be used to create a ray traveling through the volume. In the scenario, that the exemplary subvolume space skipping is not be utilized, the process may entail sampling points along this ray to determine what to render on the screen. However, since the exemplary subvolume space skipping is being utilized in this exemplary scenario with respect to method 450, the process may entail determining which subvolume the ray is about to enter. Each respective subvolume is evaluated to determine whether it should be skipped. If the subvolume is not to be skipped, the sampling proceeds along the ray. If the subvolume, is to be skipped, then the next subvolume along the path of the ray is evaluated. Since, the exemplary ray at the ray start position must be the edge of a first respective subvolume, the process may entail first taking small steps along the ray, and then rounding that position to the center of that respective subvolume. The center may then be sampled to determine whether to skip it or not.

Step 454 may entail determining whether to skip a respective subvolume of the plurality of subvolumes. In exemplary embodiments, this may entail first determining whether to skip a first subvolume closest to the ray's start position. In an exemplary embodiment, the center position of a respective subvolume may be obtained and the texture at that position may be sampled. If the sample value is lower than a threshold value, this subvolume may be skipped. If the same value is equal to or higher than a threshold value, the subvolume may not be skipped and may rendered accordingly to exemplary methods.

Step 456 may entail responsive to determining that a respective current subvolume may be skipped, performing a ray-box intersection on the subvolume's regular (not enlarged) bounds to determine where the ray would have exited this subvolume and the process may advance the ray to that position. The exit position of the respective subvolume may then be used as the respective start position for the next respective subvolume for repeating steps 454 to 458. FIG. 7A illustrates an exemplary scenarios of exemplary subvolumes utilizing regular bounds, that is, when it is determined that a respective subvolume may be skipped.

For example, in FIG. 7A, exemplary subvolumes 702 and 704 are displayed. Ray 703 is illustrated as passing through subvolumes 702 and 704. With respect to exemplary subvolume 702, to calculate an exemplary center of an exemplary subvolume, a location Near 706 (where ray 703 enters subvolume 704) may be rounded to NearCorner 708. Thereafter. Near 706 and NearCorner 708 may be compared on each axis. If the difference on an axis is positive, the next Center 712 is in the positive direction on that axis. Otherwise, the next Center 712 is in the negative direction on that axis. However, if the difference is close to zero (indicating that Near 706 and NearCorner 708 are on the same axis), a second comparison may then be made with Near+Ray_Step 710. This comparison may continue cyclically, until the Center 712 is found. Far 716 represents a point where ray 703 exits subvolume 704 and enters subvolume 702. In exemplary embodiments, this process utilizes regular bounds, that is, the bounds of the respective subvolume. Accordingly, this process requires two sets of comparison on each axis to determine Center 712 of subvolume 702. A similar set of comparisons may then be conducted to determine Center 714 of subvolume 704. In exemplary embodiments, Far 714 may serve as ray entry point for subvolume 704 and may be analogous to Near 706 for calculations Step 458 may entail responsive to determining that the respective subvolume may not be skipped, performing a ray-box intersection on an enlarged bounds to determine where the ray would have exited the enlarged bounds of the respective subvolume and advancing the ray to that position. In exemplary embodiments, the enlarged bounds may larger than the regular bounds as discussed above. Since, the process uses an exemplary enlarged bounds for this calculation, it may be assumed that the ray exit position will be entirely inside a different subvolume. In exemplary embodiments this aids in reducing oversampling artifacts when the ray crosses the edges of multiple subvolumes.

FIG. 7B illustrates an exemplary scenarios of exemplary subvolumes utilizing enlarged bounds, that is, when it is determined that a respective subvolume may be skipped.

For example, in FIG. 7B, exemplary subvolumes 702 and 704 are displayed. However, it may be assumed that in the exemplary scenario presented in FIG. 7B, subvolume 702 may not be skipped. Accordingly, enlarged bounds 720 may be utilized to determine ray start and ray stop positions for ray 703, for a respective subvolume when the subvolume may not skipped. Center 712 may still be determined utilizing the regular bounds of subvolume 702, including, for example, using Near 706. However, Far 722 represents the point that ray 703 exits enlarged bounds 720. Additionally, for rendering, in this respective scenario when subvolume 702 may not be skipped, the ray is advanced towards Far 722 while sampling the main volume texture and blending those samples together. Accordingly, for determining center 714 of subvolume 704, Far 722 of enlarged bounds 720 may be used. As is apparent, this point would be within subvolume 704, therefore, minimizing oversampling. In further detail, at the edge of exemplary cubic subvolume 702, there may be an edge of numerous cube shaped subvolumes. Additionally, Far 722 may be analogous to Near+Ray_Step 710 for purposes of calculation. Specifically, in exemplary embodiments, it is an extra voxel distance from the edge of subvolume 704, Accordingly, utilizing enlarged bounds 720 may require one set of comparison on each axis to determine an exemplary center point of a respective subvolume leading to efficiency in processing, as fewer subvolume traversals will be required on average. [Can you please expand on this]

Exemplary steps 452 to 458 may repeat until the ray finally exits the main volume, that is, the ray exit position for the main volume is reached.

In an exemplary embodiment, skipping through empty subvolumes aids in efficiency and precision of rendering by requiring less processing power and time since it skips through regions that are skippable and uses enlarged bounds to move through regions which must be rendered in a faster manner. Since, exemplary renderings may be utilized in a live surgical setting, it is imperative that such renderings are generated with high level or accuracy without any lag.

In exemplary embodiments, if color was sampled in linear color space, a gamma correction may be performed.

In exemplary embodiments, utilizing the last position of the exemplary ray, a clip position of the ray may be calculated so the volume may interact with other 3D objects in the scene. In exemplary embodiments, this calculation converts a world position (that is, an exemplary position in a real world environment) of the pixel into clipping space, which is what the rendering engine uses to determine which object to render first. Thereafter, the accumulated color and clip position may be outputted to render a three-dimensional view of the patient.

In summary, an exemplary augmented reality surgical navigation process entails at least two steps of first volumetrically rendering any radiographic imaging data onto a wireless, holographic head-mounted display. Secondly, by using optical camera depth sensing technology, precise mapping of renderings directly onto patient anatomy may be conducted by utilizing "inside-out" tracking processes.

In an exemplary embodiment, surgical instruments may be tracked in an exemplary environment using exemplary virtual cameras. Exemplary virtual cameras may represent a position from a side view of a patient being operated on. As an exemplary instrument is moved in real-life by a surgeon, the instrument's position may be calculated based on proximity data and/or position and movement information data generate from perspective of the virtual camera. Thus, a position of the exemplary virtual camera may be utilized to calculate a projection matrix, which may then be used in rendering a virtual three dimensional (3D) scene from the perspective of the virtual camera. This may be then be shown on a separate display or used as an alarm. For example, if an incision is being made too deep, an indication may be provided to the surgeon. This may be in form of an image or sound based alarm.

Systems and methods and consistent with exemplary embodiments, may be used effectively in numerous surgical subspecialties beyond neurosurgery, including orthopedic surgery, otolaryngology, and plastic surgery. Since the exemplary systems and methods may be utilized for bedside procedures as well, they may lead to significant improvements in outcomes for such procedures.

Figure 8:
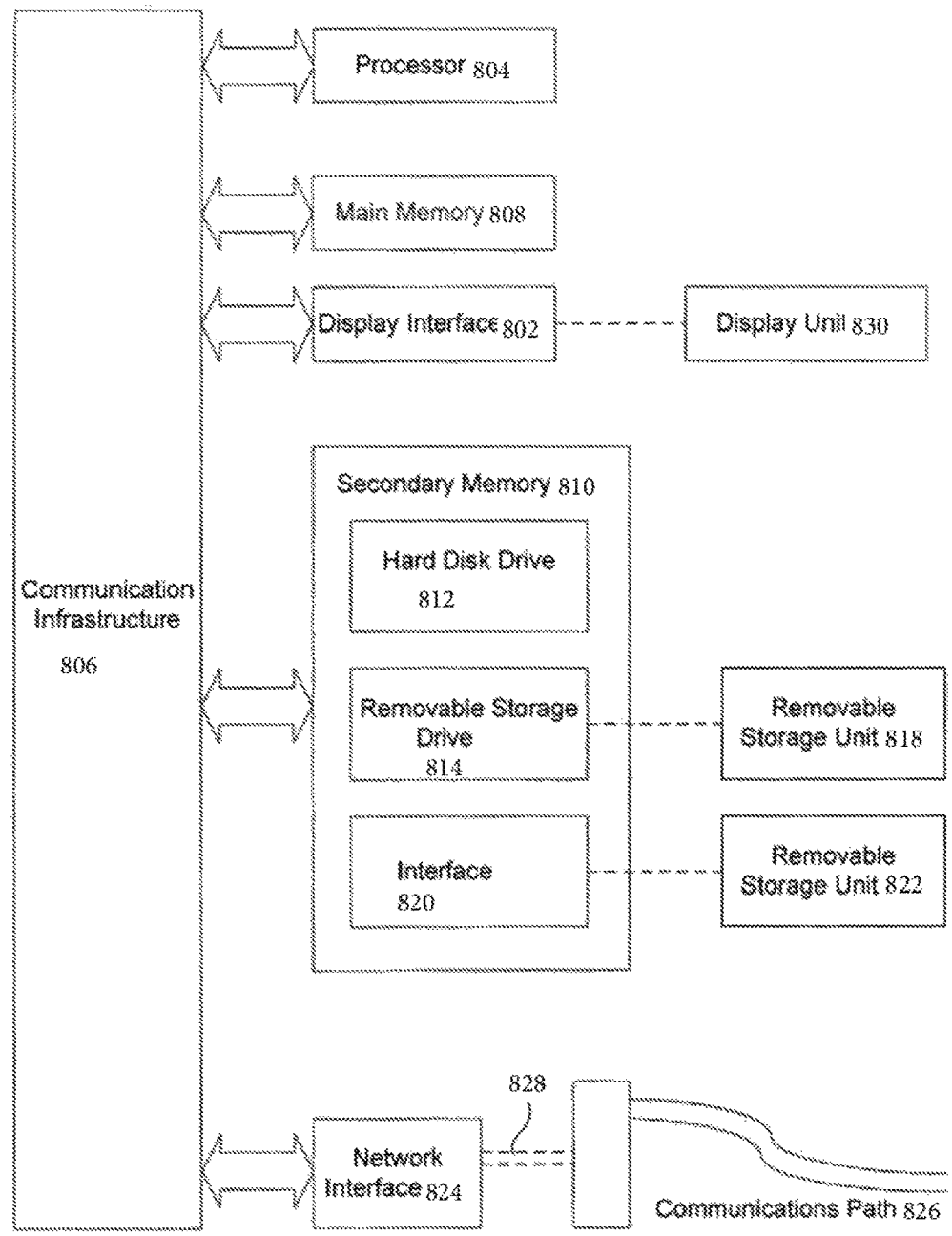
FIG. 8 illustrates an example computer system in which an embodiment of the present disclosure, or portions thereof, may be implemented as computer-readable code, consistent with exemplary embodiments of the present disclosure.

FIG. 8 illustrates an example computer system 800 in which an embodiment of the present disclosure, or portions thereof, may be implemented as computer-readable code, consistent with exemplary embodiments of the present disclosure. For example, device 100 may be implemented in computer system 800 using hardware, software, firmware, tangible computer readable media having instructions stored thereon, or a combination thereof and may be implemented in one or more computer systems or other processing systems. Hardware, software, or any combination of such may embody any of the modules and components in FIG. 1A.

If programmable logic is used, such logic may execute on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the disclosure is described in terms of this example computer system 800. After reading this description, it will become apparent to a person skilled in the relevant art how to implement the disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 804 may be a special purpose or a general-purpose processor device. As will be appreciated by persons skilled in the relevant art, processor device 804 may also be a single processor in a multi-core/multiprocessor system, such system operating alone, or in a cluster of computing devices operating in a cluster or server farm. Processor device 804 is connected to a communication infrastructure 806, for example, a bus, message queue, network, or multi-core message-passing scheme.

Computer system 800 also includes a main memory 808, for example, random access memory (RAM), and may also include a secondary memory 810. Secondary memory 810 may include, for example, a hard disk drive 812, removable storage drive 814. Removable storage drive 814 may comprise a floppy disk drive, a magnetic tape drive, an optical disk drive, a flash memory, or the like. The removable storage drive 814 reads from and/or writes to a removable storage unit 818 in a well-known manner. Removable storage unit 818 may comprise a floppy disk, magnetic tape, optical disk, etc., which is read by and written to by removable storage drive 814. As will be appreciated by persons skilled in the relevant art, removable storage unit 818 includes a computer usable storage medium having stored therein computer software and/or data.

In alternative implementations, secondary memory 810 may include other similar means for allowing computer programs or other instructions to be loaded into computer system 800. Such means may include, for example, a removable storage unit 822 and an interface 820. Examples of such means may include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 822 to computer system 800.

Computer system 800 may also include a communications interface 824. Communications interface 824 allows software and data to be transferred between computer system 800 and external devices. Communications interface 824 may include a modem, a network interface (such as an Ethernet card), a communications port, a PCMCIA slot and card, or the like. Software and data transferred via communications interface 824 may be in the form of signals, which may be electronic, electromagnetic, optical, or other signals capable of being received by communications interface 824. These signals may be provided to communications interface 824 via a communications path 826. Communications path 826 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 818, removable storage unit 822, and a hard disk installed in hard disk drive 8812. Computer program medium and computer usable medium may also refer to memories, such as main memory 808 and secondary memory 810, which may be memory semiconductors (e.g. DRAMs, etc.).

Computer programs (also called computer control logic) are stored in main memory 808 and/or secondary memory 810. Computer programs may also be received via communications interface 824. Such computer programs, when executed, enable computer system 800 to implement the present disclosure as discussed herein. In particular, the computer programs, when executed, enable processor device 504 to implement the processes of the present disclosure, such as the operations in the method illustrated by flowchart 200 of FIG. 2, flowchart 300 of FIG. 3, flowchart 400 of FIG. 4A, flowchart 450 of FIG. 4B discussed above. Accordingly, such computer programs represent controllers of the computer system 800. Where the disclosure is implemented using software, the software may be stored in a computer program product and loaded into computer system 800 using removable storage drive 814, interface 820, and hard disk drive 812, or communications interface 824.

Embodiments of the disclosure also may be directed to computer program products comprising software stored on any computer useable medium. Such software, when executed in one or more data processing device, causes a data processing device(s) to operate as described herein. An embodiment of the disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed:

1. A computer-implemented method for utilizing a virtual-three dimensional image in a real-world environment to guide medical procedures, comprising:
    receiving image data related to a patient, wherein the image data includes a plurality of Digital Imaging and Communications in Medicine (DICOM) files and associated metadata for the plurality of the DICOM files; and
    creating and displaying a three-dimensional holographic model of the patient utilizing the received image data, wherein creating a three-dimensional holographic model of the patient utilizing the received image data comprises:
        sorting the plurality of DICOM files according to an order of their physical location, wherein each of the plurality of DICOM files corresponds to a respective slice from a scan of the patient;
        acquiring raw image data for each of the respective slices associated with each of the plurality of DICOM files;
        reorienting the raw image data based on physical orientation associated with each of the respective slices and placing the raw image data for each of the respective slices in a first integer array, the first integer array containing image data associated with every slice in the scan, and splitting respective number of pixels in the first integer array associated with respective subcubes of a first size;
        creating a second integer array by splitting the first integer array into a plurality of subvolumes, wherein each respective subvolume contains a plurality of subcubes and wherein each subvolume of the plurality of subvolumes in the second integer array contains a largest value of its corresponding subcube of the first integer array;
        creating a 3D texture using the second integer array;
        creating a 3D cube mesh that is sized based on physical dimensions of the scan; and
        rendering a three-dimensional holographic model of the patient based on the 3D texture and the 3D cube mesh by utilizing ray-casting approaches.

2. The method according to claim 1, wherein rendering the three-dimensional holographic model of the patient based on the 3D texture and the 3D cube mesh by utilizing ray-casting approaches comprises:
    (i) performing a ray-box intersection test to determine a ray's start position and ray's stop position;
    (ii) determining whether to skip a respective subvolume of the plurality of subvolumes, wherein the determining whether to skip a respective subvolume of the plurality of subvolumes comprises first determining whether to skip a first subvolume closest to the ray's start position;
    (iii) responsive to determining that the respective subvolume may be skipped, performing a ray-box intersection on the respective subvolume's regular bounds to determine where the ray would have exited the respective subvolume and advancing the ray to that position;
    (iv) responsive to determining that the respective subvolume may not be skipped, performing a ray-box intersection on enlarged bounds of the respective subvolume to determine where the ray would have exited the enlarged bounds of the respective subvolume and advancing the ray to that position, wherein the enlarged bounds is larger than the regular bounds; and
    (v) repeating steps (ii to iv) for each of the plurality of subvolumes.

3. The method according to claim 2, wherein determining whether to skip the respective subvolume of the plurality of subvolumes comprises determining whether to skip the respective subvolume based on determining a value sampled of respective texture from the 3D texture at a center of the respective subvolume.

4. The method according to claim 3, wherein determining whether to skip the respective subvolume of the plurality of subvolumes comprises determining whether to skip the respective subvolume based on comparing the value sampled at a center of the respective subvolume with a threshold value.

5. The method according to claim 4, wherein the regular bounds are of a first size corresponding directly to a size of the respective subvolume and the enlarged bounds are of a second size larger than the size of the respective subvolume.

6. The method according to claim 5, wherein the second size comprises a respective voxel added for each face of the respective subvolume.

7. The method according to claim 1, further comprising: capturing data related to physical attributes of a display on which the three-dimensional holographic model is rendered, the physical attributes including positioning and movement.

8. A system for utilizing a virtual-three dimensional image in a real-world environment to guide medical procedures, the system comprising:
a processor; and
a storage device that stores a set of instructions that when executed by the processor perform a method, the method comprising:
receiving image data related to a patient, wherein the image data includes a plurality of Digital Imaging and Communications in Medicine (DICOM) files and associated metadata for the plurality of the DICOM files; and
creating and displaying a three-dimensional holographic model of the patient utilizing the received image data, wherein creating a three-dimensional holographic model of the patient utilizing the received image data comprises:
sorting the plurality of DICOM files according to an order of their physical location, wherein each of the plurality of DICOM files corresponds to a respective slice from a scan of the patient;
acquiring raw image data for each of the respective slices associated with each of the plurality of DICOM files;
reorienting the raw image data based on physical orientation associated with each of the respective slices and placing the raw image data for each of the respective slices in a first integer array, the first integer array containing image data associated with every slice in the scan, and splitting respective number of pixels in the first integer array associated with respective subcubes of a first size;
creating a second integer array by splitting the first integer array into a plurality of subvolumes, wherein each respective subvolume contains a plurality of subcubes and wherein each subvolume of the plurality of subvolumes in the second integer array contains a largest value of its corresponding subcube of the first integer array;
creating a 3D texture using the second integer array;
creating a 3D cube mesh that is sized based on physical dimensions of the scan; and
rendering a three-dimensional holographic model of the patient based on the 3D texture and the 3D cube mesh by utilizing ray-casting approaches.

9. The system according to claim 8, wherein rendering the three-dimensional holographic model of the patient based on the 3D texture and the 3D cube mesh by utilizing ray-casting approaches comprises:
(i) performing a ray-box intersection test to determine a ray's start position and ray's stop position;
(ii) determining whether to skip a respective subvolume of the plurality of subvolumes, wherein the determining whether to skip a respective subvolume of the plurality of subvolumes comprises first determining whether to skip a first subvolume closest to the ray's start position;
(iii) responsive to determining that the respective subvolume may be skipped, performing a ray-box intersection on the respective subvolume's regular bounds to determine where the ray would have exited the respective subvolume and advancing the ray to that position;
(iv) responsive to determining that the respective subvolume may not be skipped, performing a ray-box intersection on enlarged bounds of the respective subvolume to determine where the ray would have exited the enlarged bounds of the respective subvolume and advancing the ray to that position, wherein the enlarged bounds is larger than the regular bounds; and
(v) repeating steps (ii to iv) for each of the plurality of subvolumes.

10. The system according to claim 9, wherein determining whether to skip the respective subvolume of the plurality of subvolumes comprises determining whether to skip the respective subvolume based on determining a value sampled of respective texture from the 3D texture at a center of the respective subvolume.

11. The system according to claim 10, wherein determining whether to skip the respective subvolume of the plurality of subvolumes comprises determining whether to skip the respective subvolume based on comparing the value sampled at a center of the respective subvolume with a threshold value.

12. The system according to claim 11, wherein the regular bounds are of a first size corresponding directly to a size of the respective subvolume and the enlarged bounds are of a second size larger than the size of the respective subvolume.

13. The system according to claim 9, wherein the method further comprises:
capturing data related to physical attributes of a display on which the three-dimensional holographic model is rendered, the physical attributes including positioning and movement.

14. A non-transitory computer-readable medium storing a set of instructions that, when executed by a processor, perform a method, the method comprising:
receiving image data related to a patient, wherein the image data includes a plurality of Digital Imaging and Communications in Medicine (DICOM) files and associated metadata for the plurality of the DICOM files; and
creating and displaying a three-dimensional holographic model of the patient utilizing the received image data, wherein creating a three-dimensional holographic model of the patient utilizing the received image data comprises:
sorting the plurality of DICOM files according to an order of their physical location, wherein each of the plurality of DICOM files corresponds to a respective slice from a scan of the patient;
acquiring raw image data for each of the respective slices associated with each of the plurality of DICOM files;
reorienting the raw image data based on physical orientation associated with each of the respective slices and placing the raw image data for each of the respective slices in a first integer array, the first integer array containing image data associated with every slice in the scan, and splitting respective number of pixels in the first integer array associated with respective subcubes of a first size;
creating a second integer array by splitting the first integer array into a plurality of subvolumes, wherein each respective subvolume contains a plurality of subcubes and wherein each subvolume of the plurality of subvolumes in the second integer array contains a largest value of its corresponding subcube of the first integer array;

creating a 3D texture using the second integer array;

creating a 3D cube mesh that is sized based on physical dimensions of the scan; and rendering a three-dimensional holographic model of the patient based on the 3D texture and the 3D cube mesh by utilizing ray-casting approaches.

15. The non-transitory computer-readable medium according to claim 14, wherein rendering the three-dimensional holographic model of the patient based on the 3D texture and the 3D cube mesh by utilizing ray-casting approaches comprises:
  (i) performing a ray-box intersection test to determine a ray's start position and ray's stop position;
  (ii) determining whether to skip a respective subvolume of the plurality of subvolumes, wherein the determining whether to skip a respective subvolume of the plurality of subvolumes comprises first determining whether to skip a first subvolume closest to the ray's start position;
  (iii) responsive to determining that the respective subvolume may be skipped, performing a ray-box intersection on the respective subvolume's regular bounds to determine where the ray would have exited the respective subvolume and advancing the ray to that position;
  (iv) responsive to determining that the respective subvolume may not be skipped, performing a ray-box intersection on enlarged bounds of the respective subvolume to determine where the ray would have exited the enlarged bounds of the respective subvolume and advancing the ray to that position, wherein the enlarged bounds is larger than the regular bounds; and
  (v) repeating steps (ii to iv) for each of the plurality of subvolumes.

16. The non-transitory computer-readable medium according to claim 15, wherein determining whether to skip the respective subvolume of the plurality of subvolumes comprises determining whether to skip the respective subvolume based on determining a value sampled of respective texture from the 3D texture at a center of the respective subvolume.

17. The non-transitory computer-readable medium according to claim 16, wherein determining whether to skip the respective subvolume of the plurality of subvolumes comprises determining whether to skip the respective subvolume based on comparing the value sampled at a center of the respective subvolume with a threshold value.

18. The non-transitory computer-readable medium according to claim 17, wherein the regular bounds are of a first size corresponding directly to a size of the respective subvolume and the enlarged bounds are of a second size larger than the size of the respective subvolume.

19. The non-transitory computer-readable medium according to claim 14, wherein the method further comprises:

capturing data related to physical attributes of a display on which the three-dimensional holographic model is rendered, the physical attributes including positioning and movement.

* * * * *